(12) United States Patent
Shiomi et al.

(10) Patent No.: US 7,754,701 B2
(45) Date of Patent: Jul. 13, 2010

(54) DIFRUCTOSE ANHYDRIDE-CONTAINING COMPOSITION AND USE THEREOF

(75) Inventors: Takuya Shiomi, Yokohama (JP); Yasuhide Okuhara, Yokohama (JP); Akiko Tamura, Yokohama (JP); Kyoko Tomita, Yokohama (JP); Norihiro Shigematsu, Yokohama (JP); Hiroto Kikuchi, Obihiro (JP); Tsutomu Aritsuka, Obihiro (JP); Fusao Tomita, Sapporo (JP)

(73) Assignees: Fancl Corporation, Kanagawa (JP); Nippon Beet Sugar Manufacturing Co., Ltd., Tokyo (JP)

( * ) Notice: Subject to any disclaimer, the term of this patent is extended or adjusted under 35 U.S.C. 154(b) by 904 days.

(21) Appl. No.: 10/512,212

(22) PCT Filed: Apr. 24, 2003

(86) PCT No.: PCT/JP03/05245

§ 371 (c)(1),
(2), (4) Date: Sep. 2, 2005

(87) PCT Pub. No.: WO03/090759

PCT Pub. Date: Nov. 6, 2003

(65) Prior Publication Data

US 2006/0069062 A1  Mar. 30, 2006

(30) Foreign Application Priority Data

| Apr. 26, 2002 | (JP) | ............................. 2002-126021 |
| Oct. 17, 2002 | (JP) | ............................. 2002-302983 |
| Oct. 29, 2002 | (JP) | ............................. 2002-314001 |
| Nov. 11, 2002 | (JP) | ............................. 2002-326212 |
| Mar. 20, 2003 | (JP) | ............................. 2003-079129 |

(51) Int. Cl.
| A61K 31/715 | (2006.01) |
| A61K 31/70 | (2006.01) |
| A61K 9/68 | (2006.01) |
| A61K 8/00 | (2006.01) |
| A61K 8/18 | (2006.01) |
| A01N 43/04 | (2006.01) |
| A61Q 11/00 | (2006.01) |

(52) U.S. Cl. ........................... 514/54; 514/25; 514/835; 424/48; 424/49

(58) Field of Classification Search .................. 514/54, 514/25, 835; 424/48, 49
See application file for complete search history.

(56) References Cited

U.S. PATENT DOCUMENTS

| 3,914,434 | A | * | 10/1975 | Bohni | ......................... 514/738 |
| 5,057,418 | A | * | 10/1991 | Uchiyama et al. | .............. 435/99 |
| 5,296,244 | A | * | 3/1994 | Yatka | ............................. 426/3 |
| 5,633,006 | A | * | 5/1997 | Catania et al. | .............. 424/441 |
| 6,264,999 | B1 | * | 7/2001 | Yatka et al. | ..................... 426/3 |
| 6,458,828 | B1 | * | 10/2002 | Sakurai et al. | .............. 514/460 |

FOREIGN PATENT DOCUMENTS

| JP | 63-269962 | 11/1988 |
| JP | 01-285195 | 11/1989 |
| JP | 03-246296 | 11/1991 |
| JP | 04-218362 | 8/1992 |
| JP | 05-140178 | 6/1993 |
| JP | 05-146273 | 6/1993 |
| JP | 05-168419 | 7/1993 |
| JP | 05-504568 | 7/1993 |
| JP | 05-279377 | 10/1993 |
| JP | 08-214871 | 8/1996 |
| JP | 08-217784 | 8/1996 |
| JP | 10-507751 | 7/1998 |
| JP | 11-43438 | 2/1999 |
| JP | 11-155520 | 6/1999 |
| JP | 11-155564 | 6/1999 |
| JP | 2000-60541 | 2/2000 |
| JP | 2000-204042 | 7/2000 |

(Continued)

OTHER PUBLICATIONS

R. M. Francis, "Is There a Differential Response to Alfacalcidol and Vitamin D in the Treatment of Osteoporosis?" Calcif Tissue Int (1997) 60: pp. 111-114.

(Continued)

*Primary Examiner*—Shaojia Anna Jiang
*Assistant Examiner*—Scarlett Goon
(74) *Attorney, Agent, or Firm*—Knobbe Martens Olson & Bear LLP

(57) ABSTRACT

The present invention relates to a difructose anhydride (DFA)-containing composition and use thereof. DFA is a cyclic disaccharide in which the reducing termini of two fructose molecules bind each other to hydroxyl groups at the other nonreducing termini.

According to the present invention, it has been revealed that DFA is effective in accelerating the absorption of magnesium, zinc or copper, accelerating bone formation, accelerating diuretic action, and improving bowel movement and is useful in inhibiting dental caries.

A composition of the present invention can be used as a composition for a medicinal product and a food or drink product (including feed for animal use). Examples of a medicinal product and a food or drink product for human or animal use include formulated powder milk, parenteral nutrients, health food and drink products, and additives for feed and are not particularly limited as long as they are ultimately in an orally administrable form.

3 Claims, 5 Drawing Sheets

FOREIGN PATENT DOCUMENTS

JP      2002-68970      3/2002

OTHER PUBLICATIONS

Mineo, Hitoshi et al. 2001 "Various indigestible saccharides enhance net calcium transport from the epithelium of the small and large intestine of rats in vitro," Nutrient Interactions and Toxicity Research Communication, *American Society for Nutritional Sciences*, pp. 3243-3246.

Partial translation of JP 63-269962 whose English abstract is already of record.

\* cited by examiner

DIFRUCTOSE ANHYDRIDE-CONTAINING COMPOSITION AND USE THEREOF

This application is the U.S. National Phase under 35 U.S.C. §371 of International Application PCT/JP03/05245, filed on Apr. 24, 2003, which claims priority of Japanese Patent Application Nos. 2002-126021 filed on Apr. 26, 2002, 2002-302983 filed on Oct. 17, 2002, 2002-314001 filed on Oct. 29, 2002, 2002-326212 filed on Nov. 11, 2002, and 2003-79129 filed on Mar. 20, 2003. The International Application was published under PCT Article 21(2) in a language other than English.

FIELD OF THE INVENTION

The present invention relates to a difructose anhydride (DFA)-containing composition and the use thereof. More particularly, the present invention relates to the use of DFA-containing composition in accelerating the absorption of magnesium, zinc or copper, accelerating bone formation, accelerating diuretic action, improving bowel movement, and inhibiting dental caries.

DESCRIPTION OF THE RELATED ART

Despite the improvement in dietary habit, in particular, the levels of ingested magnesium, zinc, and copper by the Japanese people are lower than the nutritional requirement for them (Journal of Nutritional Science and Vitaminology Vol. 45, 519-532) and the improvement in this respect has been awaited. However, it is difficult to ingest sufficient amounts of these inorganic components without changing the current Japanese dietary habit.

Recently, an industrial method for producing an indigestible disaccharide difructose anhydride III (occasionally referred to as DFA III hereinafter) has been developed, which has made its stable supply possible. Then it has been revealed that DFA III has physiological activities such as an activity of promoting the growth of bifidobacteria (Japanese Patent Publication No. 03-5788) and an activity of enhancing calcium absorption (Japanese Patent Application Laid-open No. 11-43438). However, nothing has been known as to its activity of accelerating magnesium, zinc or copper absorption.

In view of these technological circumstances, the present inventors have newly turned their attention to the fact that it is considerably difficult to take necessary amounts of magnesium, zinc and copper by having an ordinary Japanese diet and it is extremely difficult to take them in particular for infants, the aged, and sick or recuperating patients who cannot take a sufficient amount of meals. Accordingly, the first object of the present invention is to provide a technology in which the absorption of magnesium, zinc and copper in diet into the body is enhanced; in other words, a technology in which magnesium, zinc and copper are effectively utilized in the body without increasing the amounts of these components or changing the diet components.

On the other hand, calcium taken in the daily diet is a major component of bone calcium and at the same time a kind of electrolytic ions that are essential for physiology and metabolism in blood or the like.

Generally, the Japanese are considered to be a calcium deficient people. The daily calcium requirement for a Japanese is said to be about 600 mg; however, the current average calcium intake falls below this value since it is hard to surely take sufficient amount of calcium from farm products in Japan because of the climate with a lot of rain which causes leaking of calcium from soil. Calcium cannot be appropriately taken unless meals are carefully planned since calcium is contained in limited kinds of food as shown in "Table of Food Components in Japan." The calcium intake in various countries in the world depends on the intake of dairy products. For example, in Finland where the intake of dairy products is high, the rate of accidental bone fracture is known to be low-because of high calcium intake. On the contrary, in Japan where the intake of dairy products is relatively low, calcium intake is eventually low, which results in a high rate of bone fracture.

Calcium deficiency is considered to be closely related to low bone density and the progress of osteoporosis and periodontal disease. For example, osteoporosis is a serious symptom of aging of bones which is seen worldwide in almost all ethnic groups except some exceptions. In order to prevent or treat such disorders that are caused by calcium deficiency, such as osteoporosis, a method of administering calcium derived from such calcium resources as bone powder and milk and a method of taking so-called health food, functional food, and various supplements, which contain fortified or modified calcium, have been provided to supplement the calcium intake which tends to be insufficient. However, the rate of the absorption of ingested calcium into the body is 20 to 30%, which is relatively high in babies, infants and adolescents, becomes low in adults, and in particular, radically decreases after menopause in women, which accelerates the aging of bones.

Accordingly, the administration of vitamin K or vitamin D that enhances bone formation and the administration of calcitonin, estrogen or ipriflavone that inhibits bone resorption have also been carried out as a method for preventing or treating a loss in bone density and osteoporosis caused by calcium deficiency. It is considered to be necessary to improve the calcium ingestion not only by increasing the amount of calcium intake in daily diet but also by taking a food product or medicinal composition which is effective in enhancing calcium absorption to increase the amount of calcium uptake.

As described above, it is considerably difficult to take a necessary amount of bone calcium, which is effective for the treatment of osteoporosis or the like, from an ordinary Japanese diet and it is extremely difficult to take it in particular for infants, the aged, and sick or recuperating patients who cannot take a sufficient amount of meal. Under such present circumstances, the second object of the present invention is to provide a technology in which calcium deficiency is treated not only increasing the amount of calcium intake but also by accelerating bone formation.

Further, a diuretic action is important in maintaining health and alleviating diseases in human. At present, it is an important factor in treating edema that can be caused by various reasons. Edema is a "dropsical swelling" generated by a build up of excess water caused by various reasons, including a dropsical swelling in the legs and face, "abdominal dropsy" in which water is built up in peritoneal cavity, and "pulmonary edema" in which water is accumulated in the lungs.

"Abdominal dropsy" is often generated in serious liver diseases such as cirrhosis. "Pulmonary edema" is often generated by deteriorating blood circulation caused by declining heart function due to cardiac insufficiency and the like and often associated with difficulty in breathing. Further, symptoms such as dropsical swelling and swelling of the face and eyelids due to nephrosis often appear in renal diseases. Therapeutic medicines frequently used to relieve these symptoms include "loop diuretics", "thiazide and thiazide-like hypotensive diuretics" and "potassium-sparing diuretics."

"Loop diuretics" represented by furosemide increase the urine volume by inhibiting the resorption of salt and water in the renal tubules. "Thiazide and thiazide-like diuretics" also have a similar effect and are frequently used as a hypotensive agent by enhancing the diuretic effect.

"Potassium-sparing diuretics" exert a diuretic effect without changing the potassium concentration and are expected to inhibit "hypokalemia." In particular, spironolactone has a function to inhibit the activity of an antidiuretic hormone aldosterone and is used for treating edema due to secondary aldosteronism associated with cirrhosis, nephrosis and cardiac insufficiency although its diuretic effect is not strong.

However, "electrolyte imbalance" is indicated as a side effect which is commonly found in diuretic agents. Hypokalemia is a problem in using "loop diuretics" and "thiazide and thiazide-like hypotensive agents." Further, in contrast, hyperkalemia is a problem in using "potassium-sparing diuretics." A loss of mineral balance is thus considered to be inevitable in using diuretic agents. Symptoms in low mineral conditions include fatigue, muscle weakness, constipation, and arrhythmia. Symptoms in high mineral conditions may include fatigue, arrhythmia, palpitation, short of breath, numbness in the limbs, feeling of uneasiness, and abnormal speech and behavior. The third objective of the present invention is to provide a technology in which a diuretic action can be accelerated without the mineral imbalance commonly caused by use of diuretic agents as mentioned above.

On the other hand, effect of the ingestion of oligosaccharides and dietary fibers in improving bowel movement is well known. These substances are confirmed to control the pH in the intestine, add appropriate moisture to the stool, and thus ease defecation by activating and proliferating intestinal bacteria or retaining water. Furthermore, oligosaccharides are known to accelerate peristalsis in the intestine by lower short-chain fatty acids produced by intestinal fermentation, which results in stool with an appropriate softness, moisture retention and thus smooth defecation. These substances are practically and widely used as a material for agents to improve bowel movement. For example, the effect of oligosaccharides in controlling intestinal function is shown using a drug for controlling intestinal function (Japanese Patent Application Laid-open No. 02-286058) and a health food for controlling and improving intestinal function (Japanese Patent Application Laid-open No. 63-63366).

As described, above, oligosaccharides widely known to be effective in improving bowel movement are utilized by the intestinal bacteria to condition an intestinal environment and in changing stool properties, which contributes to smooth defecation. However, effect of nonutilizable sugars, which are generally hardly utilizable by intestinal bacteria, in improving bowel movement is not known. The fourth object of the present invention is to provide a technology in which bowel movement is improved by using a composition containing DFA that is one of such nonutilizable oligosaccharides.

Further, dental caries is said to be a bacterial infection caused by bacteria called acid-producing bacteria that have a caries-inducing activity. A mechanism of generating dental caries based on this theory is as follows.

First, an enzyme glucosyl transferase produced by oral streptococci that are causative bacteria having an activity to induce dental caries, in particular *Streptococcus mutans* and *Streptococcus sobrinus* produce insoluble glucan with oral sucrose as a substrate. Next, cells of *Streptococcus mutans* and *Streptococcus sobrinus* are adhered onto the surface of teeth by the glucan produced, thereby forming cell deposit (dental plaque). In this dental plaque, various microorganisms including *Streptococcus mutans* and *Streptococcus sobrinus* grow symbiotically, organic acids are produced through the sucrose metabolism by these microorganisms, organic acids thus produced lower the pH of the surface of teeth and then demineralization of enamel surface takes place to develop dental caries. Further, the formation of dental plaque is considered to be a cause of periodontal disease and bad breath as well as dental caries. Dental caries is developed by the mechanism described above. Accordingly, in order to prevent the development of dental caries, the following measures are theoretically considered to be effective:

(1) Preventing the production of organic acids by caries inducing bacteria; and (2) Preventing the formation of dental plaque.

Thus far, sucrose substitutes, for example, xylitol (Japanese Patent Application Laid-open No. 2000-128752, Japanese Patent Application Laid-open No. 2000-53549) and palatinit (Japanese Patent Application Laid-open No. 2000-281550) have been developed as sweeteners having an activity to inhibit the induction of dental caries, and their effectiveness in inhibiting the production of organic acids and the plaque formation by dental caries causing bacteria has been revealed. Although sugar alcohols are effective only at high concentrations, they are known to induce soft stools when ingested in a large amount. Further, polyphenol, a component of green tea, has been reported and used as an agent to prevent dental caries (S. Sakanaka et al., Fragnance Journal, 11, 42-49, 1990). However, use of polyphenols is also limited because of a problem in taste.

The fifth object of the present invention is to provide a technology in which the production of organic acids by dental caries inducing bacteria is inhibited.

On the other hand, DFA is known to enhance calcium absorption at a low concentration (Japanese Patent Application Laid-open, No. 11-43438). However, it has not been found whether it can be utilized by dental caries inducing bacteria in the mouth to produce organic acids. Further, no disclosure or suggestion has been made regarding its effectiveness on the inhibition of dental caries induction in prior art.

DISCLOSURE OF THE INVENTION

The abovementioned first object can be achieved by the following first group of the invention:

1. A composition for accelerating the absorption of magnesium, zinc or copper, characterized in that it contains a difructose anhydride as an effective component.

2. The composition according to 1 above, which is a medicinal product for human or animal use.

3. The composition according to 1 above, which is a food or drink product for human or animal use.

The abovementioned second object can be achieved by the following second group of the invention:

4. An oral composition for accelerating bone formation, characterized in that it contains a difructose anhydride as an effective component.

5. The composition according to 4 above, characterized in that it further contains one or more of calcium, magnesium, phosphorus, isoflavone, vitamin K or vitamin D.

6. The composition according to 4 or 5 above, which is a medicinal product for human or animal use.

7. The composition according to 4 or 5 above, which is a food or drink product for human or animal use.

8. Use of a difructose anhydride as an oral composition for accelerating bone formation.

The abovementioned third object can be achieved by the following third group of the invention:

9. An oral composition having a diuretic effect, characterized in that it contains a difructose anhydride.

10. A diuretic, characterized in that it contains a difructose anhydride.

The abovementioned fourth object can be achieved by the following fourth group of the invention:

11. A composition for improving bowel movement, characterized in that it contains a difructose anhydride and/or melibiose.

12. A method for improving bowel movement comprising administering the composition according to 11 above.

The abovementioned fifth object can be achieved by the following fifth group of the invention:

13. A composition for inhibiting the induction of dental caries, characterized in that it contains a difructose anhydride as an effective component.

14. The composition according to 13 above, characterized in that it further contains one or more components selected from the group consisting of xylitol, maltitol, palatinit, mannitol, sorbitol, palatinose, panose oligosaccharides, lactitol, erythritol, coupling sugars, and isomalto-oligosaccharides.

15. The composition according to 13 or 14 above, which is an oral composition for human or animal use.

16. The composition according to 13 or 14 above, which is a medicinal product for human or animal use.

17. The composition according to 13 or 14 above, which is a food or drink product or feed for human or animal use.

18. Use of a difructose anhydride as a composition for inhibiting the induction of dental caries.

According to the first group of the invention, an effect of accelerating the absorption of Mg, Zn, or Cu can be obtained by using DFA and thus the absorption of these minerals into the body can be safely and greatly accelerated.

According to the second group of the invention, bone formation can be greatly accelerated.

According to the third group of the invention, a diuretic effect can be safely realized without any side effect.

According to the fourth group of the invention, stool properties can be improved so that the deterioration of health associated with defecation can be restored.

According to the fifth group of the invention, a composition which can greatly inhibit dental caries can be provided.

BEST MODE FOR CARRYING OUT THE INVENTION

Figure 1:
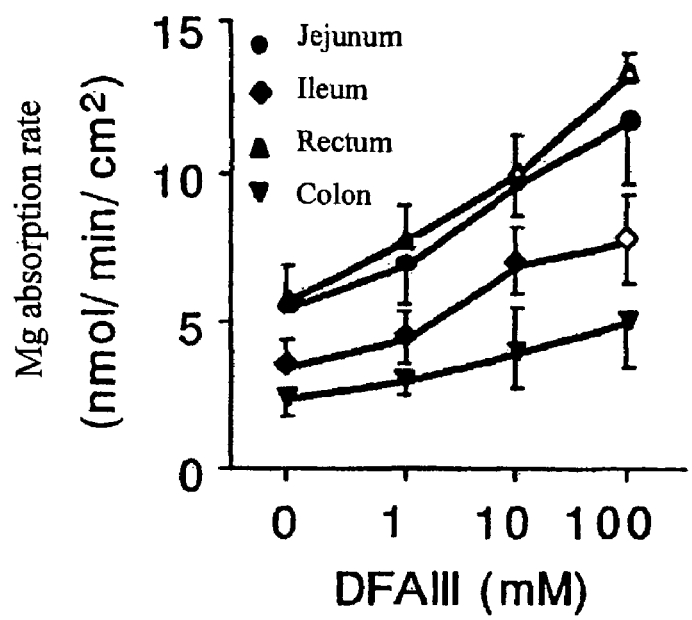
FIG. 1 shows the acceleration of magnesium absorption by DFA III in the jejunum, ileum, cecum, and colon.

DFA according to the present invention means a cyclic disaccharide in which the reducing termini of two fructose molecules bind each other to hydroxyl groups at the other nonreducing termini. While DFA is conventionally known to be found in caramel, honey and the like, it can be industrially manufactured by fermenting inulin with an inulin hydrolyzing enzyme such as inulinase (EC 3.2.1.7) and inulase (EC 2.4.1.93), or a microorganism which produces CFTase that cleaves 6-8 molecules of fructose for cyclization, such as *Arthrobacter* sp. H 65-7 strain and *Arthrobacter* sp. AHU 1753 strain. There are five derivatives with different modes of linkage between two fructose molecules; they are called DFA I, DFA II, DFA III, DFA IV, and DFA V, respectively. Although DFA according to the present invention refers to all of them, DFA III and DFA IV are preferably used and DFA III is more preferably used in the present invention. The reason is that DF III is excellent in efficiency in industrial production and in stability and the like after purification, whereas DFA I, DFA II and DFA IV may be poor in stability as a disaccharide and possibly deteriorate due to moisture absorption or deliquescence and generate problems in handling for practical use.

Of course, DFA of the present invention is not limited by production methods described above. Further, DFA can be used together with melibiose. Alternatively, melibiose alone can be administered.

Melibiose is one of natural sugars having an α-galactosyl linkage, namely a disaccharide in which galactose and glucose are combined in an α (1-6) linkage. In nature, melibiose is confirmed to be contained in soybeans and root vegetables and is also known to be found in honey from violet flowers, Chinese milk vetch and the like. A typical example of a method of the industrial production comprises the steps of cooling molasses produced in the process of sugar extraction from beats, isolating raffinose by crystallization, fermenting with baking yeast and utilizing fructose, a component sugar of raffinose. Further, a method of the extraction and isolation from a natural product such as honey can be used.

Naturally, DFA and melibiose to be used in the present invention are not limited to those produced by the methods described above.

A composition of the present invention can be used as a composition for a medicinal product and a food or drink product (including feed for animal use). Examples of a medicinal product and a food or drink product for human or animal use include formulated powder milk, parenteral nutrients, health food and drink products, and additives for feed and are not particularly limited as long as they are ultimately in an orally administrable form. The DFA content is not particularly limited but it is generally 0.1 to 99% by weight of the composition.

Further, a composition for accelerating the absorption of magnesium, zinc or copper can be used together with other materials having an activity for accelerating mineral absorption, such as maltitol, lactose, fructooligosaccharides, casein phosphopeptide (CPP), and brewery yeast cell wall.

An oral composition for accelerating bone formation may further contain one or more of calcium, magnesium, phosphorus, isoflavone, vitamin K and vitamin D that are known to have an activity for accelerating bone formation.

When used as a food or drink type composition, DFA or its processed product can be appropriately used as it is or together with other food products or food components according to an ordinary method. The processed product broadly means a processed food product containing said food product, ranging from obvious food products (food products in the narrow sense) to tablets or the like. Further, in processing, a conventional method for processing food products can be applied without difficulty because of its high heat stability and high acid stability. A composition of the present invention is not particularly limited to the form of powder, granules, paste, liquid, suspension, and the like and can be, for example, formulated into a health drink using various components generally used in manufacturing health drinks, such as a sweetener, sour agent, and vitamin compounds.

When used as a medicinal composition, this effective component is administered in various forms. For example, it can be administered orally in a form of tablets, capsules, granules, powder, syrup, and the like. These various formulations can be formulated according to a conventional method by adding known auxiliaries generally used in the technological field of medicinal preparation, such as an excipient, binder, disintegrator, lubricant, flavoring agent, dissolution agent, suspending agent, and coating agent, to a main ingredient.

The amount to be used varies depending on symptoms, age, body weight, method of administration and drug form; however, when used for accelerating the absorption of magnesium, zinc, or copper or accelerating bone formation, the amount of daily administration for an adult per 1 kg body weight may usually be 0.01 mg to 1000 mg for intravenous administration, 0.01 mg to 1000 mg for intramuscular administration, and 0.5 mg to 2000 mg, preferably 1 mg to 1000 mg, for oral administration.

When used as a diuretic agent, the amount is 1 to 10 g per day. No effect is observed with the amount of less than 1 g and symptoms such as softening stool can be occasionally observed with the amount of more than 10 g. However, since the softening stool can be affected by individual's physical constitution, daily diet and the like, ingestion in the amount of more than 10 g is not necessarily strictly prohibited, and thus it is necessary to increase or decrease the amount by monitoring individual's condition. In any case, DFA has no toxicity problem since it is a safe sugar food product and thus a diuretic effect can be safely obtained without serious side effects, such as anaphylaxis, allergy, disturbance of consciousness, aplastic anemia, and subcutaneous bleeding and notable side effects, such as liver disorder and rash, which are commonly seen with diuretic agents generally used.

When used for improving bowel movement, the bowel movement in a human can be improved by directly drinking DFA or by taking a DFA-containing food. The amount of ingestion is in the range from about 1 to 10 g, preferably from about 3 to 5 g, which is similar to that for other common trisaccharides. Further, mode of ingestion is not particularly limited and it can be taken as it is, as a solution in water, or as a processed food product. DFA has a characteristic fresh sweetness and can be taken as it is without difficulty. Further, it can be admixed into a food product without difficulty using an ordinary food processing method because of its high heat stability and acid stability. When ingested, characteristically, these disaccharides are partly utilized by intestinal bacteria, in particular bifidobacteria, or hardly utilized and moved into the blood stream to be decomposed and metabolized in the liver.

Now, osteocalcin is a matrix protein produced and released by differentiated osteoblasts, known to increase its concentration in blood with the acceleration of bone formation, and is useful as an indicator that specifically reflects bone formation. Accordingly, it is widely used as one of osteogenic markers in blood and urine, for the purpose of studying the change in bone metabolism in osteoporosis in the clinical field and the effectiveness on the prevention and treatment of bone mass loss. Calcium taken up into the body is released into the blood stream from the intestinal tract and then surely absorbed and immobilized as bone calcium, thereby ultimately improving bone density. In the present invention, it has been confirmed that the concentration of osteocalcin in blood, one of bone formation markers, is increased by administering a DFA-containing oral composition together with calcium. This finding shows that DFA significantly accelerates calcium absorption, improves the rate of calcium utilization in the body and thus can make an oral composition having an excellent activity for accelerating bone formation. Further, even when DFA alone is ingested, the increase in the osteocalcin concentration and the acceleration of bone formation are similarly confirmed. These results indicate that a DFA-containing composition is effective in accelerating calcium absorption and is furthermore a useful composition to potentially accelerate bone formation.

Further, DFA is a disaccharide that can be used as a food product and its greatest character known at present is its function in mineral absorption. DFA has an effect for accelerating the absorption of calcium, potassium and the like. Further, while ordinary sugars accelerate mineral absorption through a mechanism in which minerals are dissolved and become readily absorbable by activating intestinal bacteria and lowering intestinal pH, DFA is reported to accelerate the absorption by taking up minerals into the body via tight junctions in the intestinal tract, besides through such mechanism. Further, characteristically, this action accelerates absorptive function of the body when minerals are deficient, while it inhibits absorptive function of the body when minerals are excessive. Namely, the present inventors have found that DFA having such a mineral absorptive function has a diuretic effect.

A composition according to the present invention can enhance a diuretic effect without generating low mineral or high mineral conditions which are common to existing diuretic agents by the reasons described above. In the present invention, a DFA-containing composition is produced and orally or non-orally administered to a human expecting to benefit from a diuretic effect. A composition of the present composition can be made into any ultimate form as long as it is orally or non-orally ingestible.

Although the reason why DFA can improve defecation is still poorly understood, the effect on the growth of bifidobacteria in the upper layer of the intestine or on gaps between intestinal cells and the effect on water absorption by the effect of ionic gradient are suggested among others. Further, since the effect on improving defecation is exhibited in an extremely early stage, an action attributed to change in the shape of the cells through intestinal cells and tight junctions is also suggested, as well as the effect of utilization by intestinal bacteria. Furthermore, utilization by particular intestinal bacteria is also suggested to contribute.

Next, an inhibitory effect on dental caries is to be explained.

*Streptococcus mutans* is known to be a causative bacterium for early stage dental caries because of its ability to strongly adhere to teeth and to produce acids. Generally, in dental caries caused by such a causative bacterium, the presence of sucrose is a key factor for the induction of dental caries. Namely, a large amount of organic acid is produced from sucrose and lowers the pH in the mouth, and consequently the enamel surface is demineralized to generate or develop dental caries. It is considered to be one way of preventing dental caries to inhibit the acid production by these causative bacteria from sucrose. When the bacteria were cultured in a medium containing a DFA-containing composition of the present invention, the acid production was decreased and the decrease in pH was inhibited. Further, it has been found that the acid production is more effectively inhibited by using DFA together with a small amount of sugar alcohol with which the effect of preventing dental caries is recognized but diarrhea is reportedly caused when ingested in a large amount. The abovementioned findings show that a DFA-containing composition of the present invention inhibits the acid production by bacteria that cause dental caries and can thus make a composition having an excellent dental caries inhibiting activity.

A composition according to the present invention contains DFA as an effective component and can be used as an oral composition and a composition for a medicinal product or food or drink product (including feed for animal use). Examples of an oral composition for human or animal use include a tooth powder, moist tooth-cleansing agent, toothpaste, fluid tooth-cleansing agent, liquid tooth-cleansing agent, mouthwash, and mouth-refreshing rinse. Examples of a medicinal product and food or drink product include a powdered milk formula, enteral nutrient, health food or drink product, feed additive, and confectionary, and are not particularly limited as long as they are in an orally ingestible form.

The content of DFA is not particularly limited; however, expected effect can generally be achieved with a content of 0.1 to 99% of the composition. Further, a composition of the present invention can contain one or more kinds of substances that are known to have an activity to inhibit dental caries induction, such as xylitol, maltitol, palatinit, mannitol, sorbitol, palatinose, panose oligosaccharide, lactitol, erythritol, coupling sugars and isomalto-oligosaccharide.

When used as an oral composition, besides the abovementioned components, components that are generally mixed with an oral composition can be appropriately mixed within a range not to damage the present invention, depending on dosage forms.

For example, an abrasive agent, wetting agent, thickening agent surfactant, perfume, sweetening agent, coloring agent, antiseptic, pH controlling agent, and various medicinally effective components can be mixed within a range not to damage the effect of the present invention.

Examples of an abrasive agent include aluminum oxide, aluminum hydroxide, aluminum silicate, zirconium silicate, anhydrous silicate, precipitating silica, silica gel, calcium carbonate, calcium pyrophosphate, dibasic calcium phosphate, calcium phosphate, tricalcium phosphate, hydroxyapatite, fluoroapatite, halogenized apatite, magnesium carbonate, magnesium phosphate, insoluble sodium methacrylate, insoluble calcium methacrylate, titan oxide, zeolite, and synthetic resin abrasives.

Examples of a wetting agent include sugar alcohols such as sorbitol, maltitol, xylitol, and lactitol, and polyalcohols such as glycerin, 1,3-butylene glycol, 1,2-pentanediol, polyethylene glycol, polypropylene glycol, and dipropylene glycol.

Examples of a thickening agent include carboxyvinyl polymers, sodium carboxymethyl cellulose, methyl cellulose, hydroxyethyl cellulose, caragenan, alkali metal alginates such as sodium alginate, gums such as duran gum xanthan gum, guar gum, tragacanth gum, karaya gum, bee gum, and arabia gum, polyvinyl alcohol, polyvinyl pyrrolidone, silica gel, and aluminium silica gel.

Examples of a surfactant include anionic surfactants, cationic surfactants, amphoteric surfactants, and nonionic surfactants, and more particularly, alkyl sulfates, alkylbenzene sulfonates, sucrose fatty acid esters, lactose fatty acid esters, lauroyl sarcosinate, N-acyl glutamate, α-olefin sulfonate, 2-alkyl-N-carboxyl-N-hydroxyethyl imidazolium betaine, N-acyl taurinate, alkylol amides, polyoxyethylene sorbitan fatty acid esters, polyoxyethylene hydrogenated castor oil or its fatty acid esters, polyglycerin fatty acid esters, sorbitan fatty acid esters, fatty acid esters, polyethylene glycol fatty acid esters, and propylene glycol fatty acid esters.

Examples of perfume include menthol, peppermint oil, spearmint oil, orange oil, lemon oil, eucalyptus oil, Japanese mint oil, acacia oil, funnel oil, bitter almond (*Prunus amygdalus*) oil, calamus oil, camphor oil, cinnamon oil, cassia oil, cinnamon leaf oil, rose flower oil, sandal wood oil, clove oil, herb oil, banana oil, apple oil, methyl salicylate, carvone, anethol, terpenes such as limonene, and compound perfume.

Examples of a sweetening agent include saccharine, sodium saccharine, xylitol, stevioside, stevia extract, rebaudioside, para-methoxy cinnamic aldehyde, neohesperidyl dihydroxychalcone, perillartine, thaumatin, glycyrrhizin, glycyrrhizin monoglucoside, hemandulcin, trehalose, aspartame, and sorbit.

Examples of a coloring agent include statutory pigments such as Blue No. 1 and Yellow No. 4, titanium dioxide, and caramel.

Examples of an antiseptic agent include para-oxybenzoic acid esters, benzoates, alkyldiaminoethylglycine hydrochloride, and phenoxyethanol.

Examples of a pH controlling agent include organic acids such as citric acid, malic acid, phosphoric acid and acetic acid, and salts thereof, sodium carbonate, sodium hydrogen carbonate, potassium carbonate, potassium hydrogen carbonate, calcium carbonate, calcium hydrogen carbonate, ammonium carbonate, ammonium hydrogen carbonate, potassium sodium carbonate, lithium carbonate, urea, amino acid oligomers, sodium chloride, inorganic calcium such as calcium chloride, calcium nitrate, calcium sulfate, calcium glycerophosphate, and calcium hydroxide, calcium salts of organic acids such as calcium lactate, calcium acetate, calcium malonate, calcium citrate, calcium glyconate, calcium glycerinate, calcium tartarate, and calcium phytate.

Examples of a medicinally effective component include allantoin, tocopherol acetate, isopropyl methylphenol, glycyrrhizinic acids, glytyl retinoates, dextrase, chlorophyll, sodium copper chlorophyll, flavonoid, tranexamic acid, mutanase, lysozyme, amylase, protease, lytic enzymes, superoxide dismutase, epsilon aminocaproic acid, aluminum allantoinate, aluminum chlorohydroxy allantoinate, dihydrocholestanol, bisabolol, glycerophosphate, water soluble inorganic phosphoric acid compounds, fluorides such as sodium fluoride, sodium monofluorophosphate, stannous fluoride, potassium fluoride, sodium fluosilicate, aluminum fluoride, silver fluoride, hexylamine hydrofluoride, decanolamine hydrofluoride and octadecenylamine hydrofluoride, edetic acid, zinc citrate, zinc chloride, copper gluconate, chlorhexidine gluconate, copper chloride, polyphosphates, pyrophosphates, vitamins such as vitamins A, C, E, and $B_6$ and pantothenates, amino acids such as glycine, lysine and histidine, sodium chloride, sodium bicarbonate, aluminum lactate, potassium nitrate, sarcosinate, polyphenol compounds such as catechins, and crude drugs.

Other ingredients such as ethanol, water, silicone substances, sugar alcohols, and natural extracts can be appropriately mixed. Further, the amount of ethanol to be mixed is preferably 5 to 10% by weight.

An oral composition of the present invention can be prepared by admixing the components described above and making into various forms according to an ordinary method.

When used as a food or drink product, DFA or its processed product can be appropriately used as it is or together with other food products or food components according to an ordinary method. The processed product broadly means a processed food product containing said food product, ranging from obvious food products (food products in the narrow sense) to tablets or the like. Further, in processing, a conventional method for processing food products can be applied without difficulty because of its high heat stability and high acid stability. A composition of the present invention is not particularly limited to the form of powder, granules, paste, liquid, suspension, or the like. For example, it can be formulated into a health drink using various components generally used in manufacturing health drinks, such as a sweetener, sour agent, and vitamin compounds or into a tableted candy-like composition.

For example, a tableted candy-like product can be provided as a confectionery such as chewing gum, candy, tableted candy, jelly and gummi candy. A tableted candy-like composition can be manufactured by mixing ingredients including DFA and sugar alcohol with stirring using a kneader. Further, various sugar sweeteners such as maltose and reduced glutinous starch syrup, and highly sweet sweeteners such as luohanguo extract, aspartame, and stevioside can be added.

When used as a medicinal composition, this effective component is administered in various forms. For example, it can be administered orally in a form of tablets, capsules, granules, powder, syrup, and the like. These various formulations can be formulated according to a conventional method by adding known auxiliaries generally used in the technological field of medicinal preparation, such as an excipient, binder, disintegrator, lubricant, flavoring agent, dissolution agent, suspending agent, and coating agent, to a main ingredient. The amount to be used varies depending on symptoms, age, body weight, method of administration and drug form; however, generally, the amount of daily administration for an adult per 1 kg body weight may be 0.01 mg to 1000 mg for intravenous administration, 0.01 mg to 1000 mg for intramuscular administration, and 0.5 to 2000 mg, preferably 1 to 1000 mg, for oral administration.

It has not been known at all that DFA cannot be metabolized by oral bacteria so that no organic acid is produced, which is a new finding obtained by the present invention.

Further, DFA, an effective component of the invention, has no problem in its safety. Results of an acute toxicity test with DFA III carried out using mice for 10 days showed no death even with 1000 mg/kg of oral administration.

Example 1

Acceleration of magnesium absorption by DFA III was confirmed by using an Ussing chamber as follows.

In this experiment, 7 to 8 weeks old Sprague-Dawley male rats (with an average body weight of about 260 g) were used.

The rats were purchased at 6 weeks of age (Japan SLC) and fed on a commercial solid feed (CE-2, Japan CLEA) until the start of the experiment.

On the day of the experiment, rats were injected intraperitoneally with sodium pentobarbital and the small intestines (cejunum and ileum) and the large intestines (cecum and colon) were extracted under the anaesthetization. Contents of each of the intestines were removed, the intestines were opened, and the serous membrane and the layer of smooth muscle were peeled off to prepare a specimen comprising the mucous membrane and submucosal tissue, which was then loaded onto an Ussing chamber (with an effective area of 0.67 $cm^2$).

Separately, a buffer solution for the mucous membrane side and a buffer solution for serous membrane side were prepared. The buffer solution for mucous membrane side was basically comprised of the following ingredients. The ion concentration upon measuring the rate of Mg absorption was adjusted to 0.625 mM and buffer solutions with DFA III concentrations of 0, 1, 10, and 100 mM were prepared for the test. A buffer solution without DFA III (0 mM) was prepared as a control.

| Buffer solution for mucous membrane side: (30 mM HEPES buffer solution, pH 7.4) | |
|---|---|
| NaCl | 125 mM |
| KCl | 14 mM |
| L-Glutamine | 6 mM |
| $MgCl_2 \cdot 6H_2O$ | 0.625 mM |
| HEPES | 30 mM |
| DFA III | 0 to 100 mM |

The buffer solution for serous membrane side was basically comprised of the following ingredients and the ionic concentration was adjusted to 1 mM upon measuring the rate of Mg absorption.

| Buffer solution for serous membrane side: (30 mM HEPES buffer solution, pH 7.4) | |
|---|---|
| NaCl | 125 mM |
| KCl | 14 mM |
| L-Glutamine | 6 mM |
| $MgCl_2 \cdot 6H_2O$ | 1 mM |
| HEPES | 30 mM |

The whole chamber system was heated to 37° C. and incubation was carried out with 100% $O_2$ passing through the solutions of mucous membrane side and serous membrane side for 30 minutes.

After the incubation was completed, the solution of serous membrane side was recovered and the Mg concentration in the solution was measured using a commercial kit (Wako Pure Chemicals). The net rate of mineral absorption from the mucous membrane side to the serous membrane side per minute was obtained from the increase in the Mg concentration and shown as a value per unit area of the intestinal tract. The experiment was repeated 6 heads for each group.

Results obtained are shown in FIG. 1. The Mg absorption evidently increased with an increase of the DFA III concentration.

Example 2

The rate of zinc absorption was measured in the same manner as described in Example 1, except that 0.0125 mM $ZnSO_4$ heptahydrate was used for 1 mM $MgCl_2$ hexahydrate and the ion concentration was adjusted to 0.0125 mM upon measuring the rate of Zn absorption in a buffer solution for mucous membrane side and that 1 mM $ZnSO_4$ heptahydrate was used in a buffer solution for serous membrane side.

Figure 2:
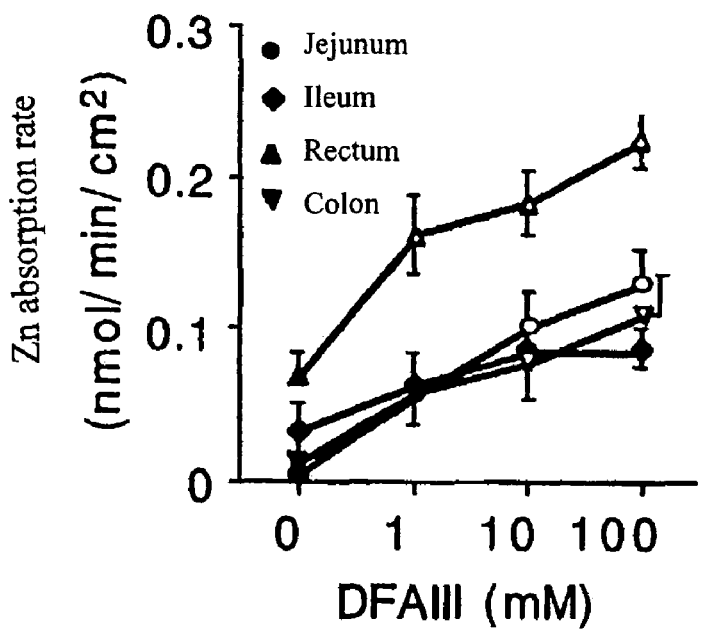
FIG. 2 shows the acceleration of zinc absorption by DFA III in the jejunum, ileum, cecum, and colon.

Results obtained are shown in FIG. 2. The Zn absorption evidently increased with an increase of the DFA III concentration.

Example 3

The rate of cupper absorption was measured in the same manner as described in Example 1, except that 0.0125 mM $CuCl_2$ dihydrate was used for 1 mM $MgCl_2$ hexahydrate and the ion concentration was adjusted to 0.0125 mM upon measuring the rate of Cu absorption in a buffer solution for mucous membrane side and that 1 mM $CuCl_2$ dihydrate was used in a buffer solution for serous membrane side.

Figure 3:
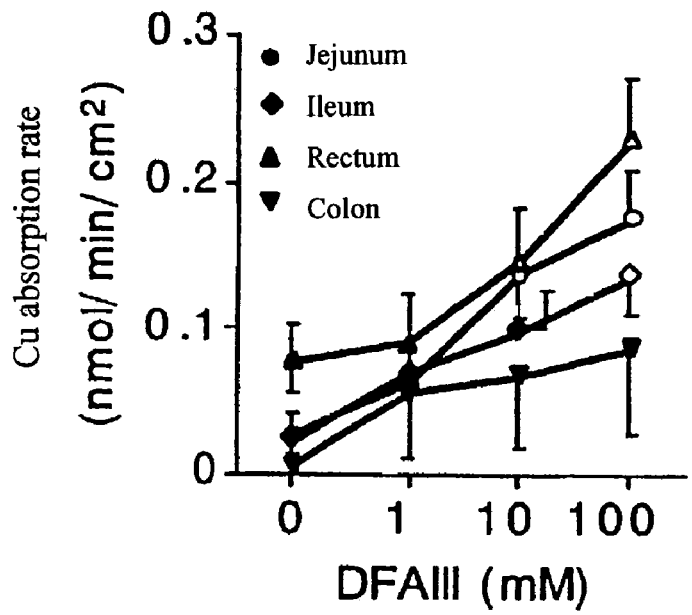
FIG. 3 shows the acceleration of copper absorption by DFA III in the jejunum, ileum, cecum, and colon.

Results obtained are shown in FIG. 3. The Cu absorption evidently increased with an increase of the DFA III concentration.

Example 4

Effectiveness of DFA on bone formation in human was studied.

Figure 4:
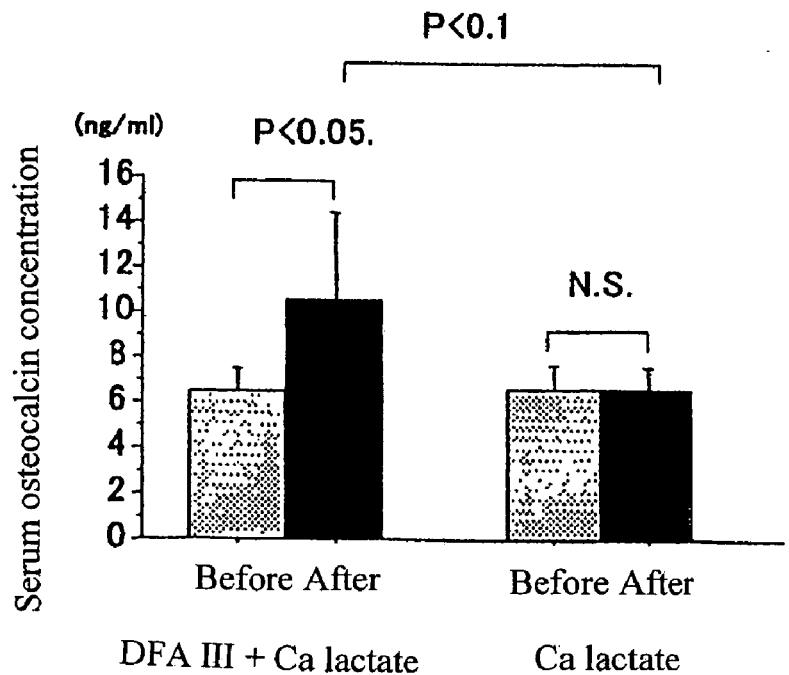
FIG. 4 shows change in the serum osteocalcin concentration before and after the administration of 3 g of DFA III and 0.77 g of calcium lactate, or 0.77 g of placebo (calcium lactate) 3 times a day for 1 weeks.

Six healthy adult males were administered with 3 g of DFA III and 0.77 g of calcium lactate or 0.77 g of placebo (calcium lactate) 3 times a day for 1 week to study the change in serum osteocalcin concentration. Results obtained are shown in FIG. 4. As evident from the results, it was confirmed that when DFA was administered together with calcium, the level of osteocalcin, an index for bone formation, increased more than when calcium alone was administered.

Example 5

Effectiveness of DFA on bone formation in human was studied.

Figure 5:
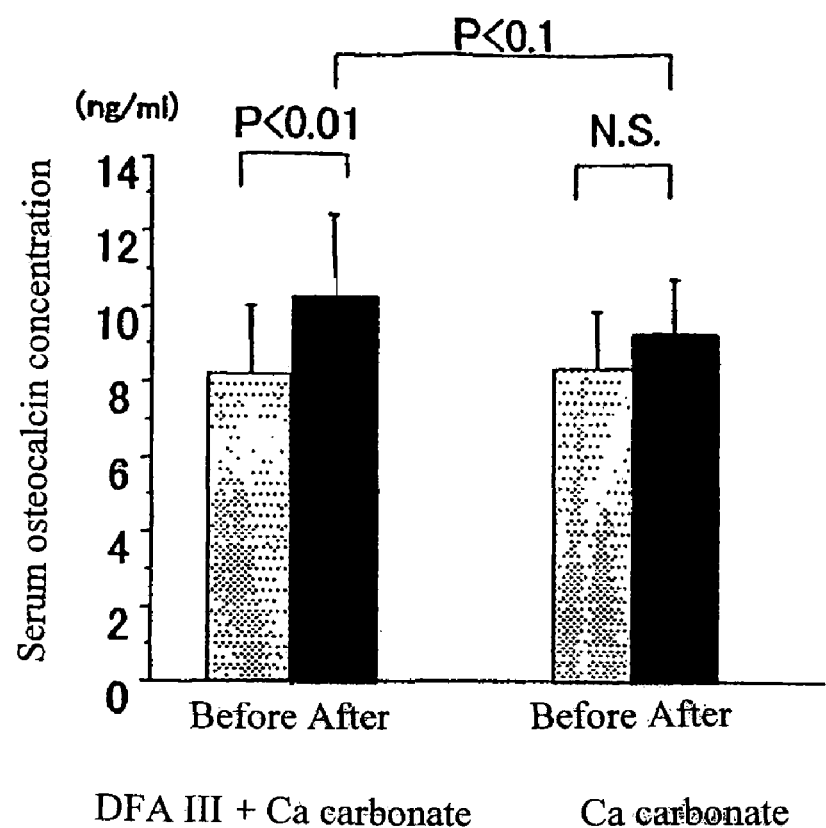
FIG. 5 shows change in the serum osteocalcin concentration before and after the administration of 1 g of DFA III and 0.25 g of calcium carbonate, or 0.25 g of placebo (calcium carbonate) 3 times a day for 2 weeks.

Fourteen healthy adult males were administered with 1 g of DFA III and 0.25 g of calcium carbonate or 0.25 g of placebo (calcium carbonate) 3 times a day for 2 weeks to study the change in serum osteocalcin concentration. Results obtained are shown in FIG. 5. As evident from the results, it was confirmed that when DFA was administered together with calcium, the level of osteocalcin, an index for bone formation, increased more than when calcium alone was administered.

Example 6

Effectiveness of DFA on bone formation in human was studied.

Twenty-three healthy adult males and females on normal diet were administered with 3 g of DFA III 3 times a day for 2 weeks to study the change in serum osteocalcin concentration. Results obtained are shown in Table 1 below.

As evident from the results in Table 1, it was confirmed that the level of osteocalcin, an index for bone formation, was increased by the ingestion of DFA.

TABLE 1

|  | After ingestion | Before ingestion |
|---|---|---|
| Serum osteocalcin concentration (ng/ml) | 5.7 ± 1.5 | 7.0 ± 2.0* |

(Average ± SD)
*p < 0.1

Example 7

Diuretic Test Using DFA III

DFA III was made into granules to make a granular food product. Since granulation was possible without excipient, the DFA content was 100%. Six healthy males were given with 1 g/day of this granular food product together with water consecutively for 1 week in the first period of the test. Then, after a week of the washout period, the same 6 healthy subjects were given with 1 g/day of sugar together with water consecutively for 1 week in the second period of the test.

During the test periods, all subjects lived under the same environment, doing the same level of exercise and taking the same amount of diet and drinking water. The whole volume of urine excreted during the test periods was recovered and the volume was measured to obtain a daily average urine volume to compare the two test periods. Results are shown in Table 2.

TABLE 2

Results of test for diuretic effect of DFA

|  |  | Volume of urea (average per day) | |
|---|---|---|---|
|  |  | First test period | Second test period |
| Subject | A | 2560 ml | 1650 ml |
|  | B | 2850 ml | 1250 ml |
|  | C | 3010 ml | 1850 ml |
|  | D | 2050 ml | 1520 ml |
|  | E | 2600 ml | 1620 ml |
|  | F | 2950 ml | 1760 ml |

As shown above, in all individual subjects, the average of the daily urine volume in the first test period when the composition of the invention was given was evidently greater than that in the second test period when sugar was given. Further, results of biochemical blood tests which were simultaneously carried out showed that values for the liver function test, renal function test, blood pressure, blood cell counts, total Chol (cholesterol value), and TG (triglycerides value) were the same in the first test period and the second test period and no abnormal subjective findings were reported.

Example 8

Effectiveness on defecation in human was studied.

Fifty adults who were healthy but aware of their poor stool frequency and tendency of constipation were given with 3 g of DFA III, 3 g of melibiose or 3 g of placebo (starch) once a day for one month. The defecation condition was recorded and stool properties and feeling of defecation were studied. Results are shown in Tables 3 and 4.

TABLE 3

Stool properties

| | Change observed | | | | | |
|---|---|---|---|---|---|---|
| Group given with: | Diarrhea | Soft stool | Normal stool | Solid stool | Constipation | No change |
| 3 g of DFA III | 0 | 7 | 39 | 3 | 0 | 0 |
| 3 g of melibiose | 0 | 8 | 40 | 2 | 0 | 0 |
| 3 g of placebo | 0 | 0 | 0 | 3 | 0 | 47 |

Note:
In the table, constipation means that the constipation being aware of before ingestion becomes worse after ingestion.

TABLE 4

| | Feeling of defecation | | | | |
|---|---|---|---|---|---|
| Group given with: | Worse | Slightly worse | No change | Slightly better | Much better |
| 3 g of DFA III | 0 | 0 | 0 | 27 | 23 |
| 3 g of melibiose | 0 | 0 | 0 | 28 | 22 |
| 3 g of placebo | 1 | 2 | 45 | 2 | 0 |

Example 9

Effect of DFA in Inhibiting Acid Production by *Streptococcus mutans*

Figure 6:
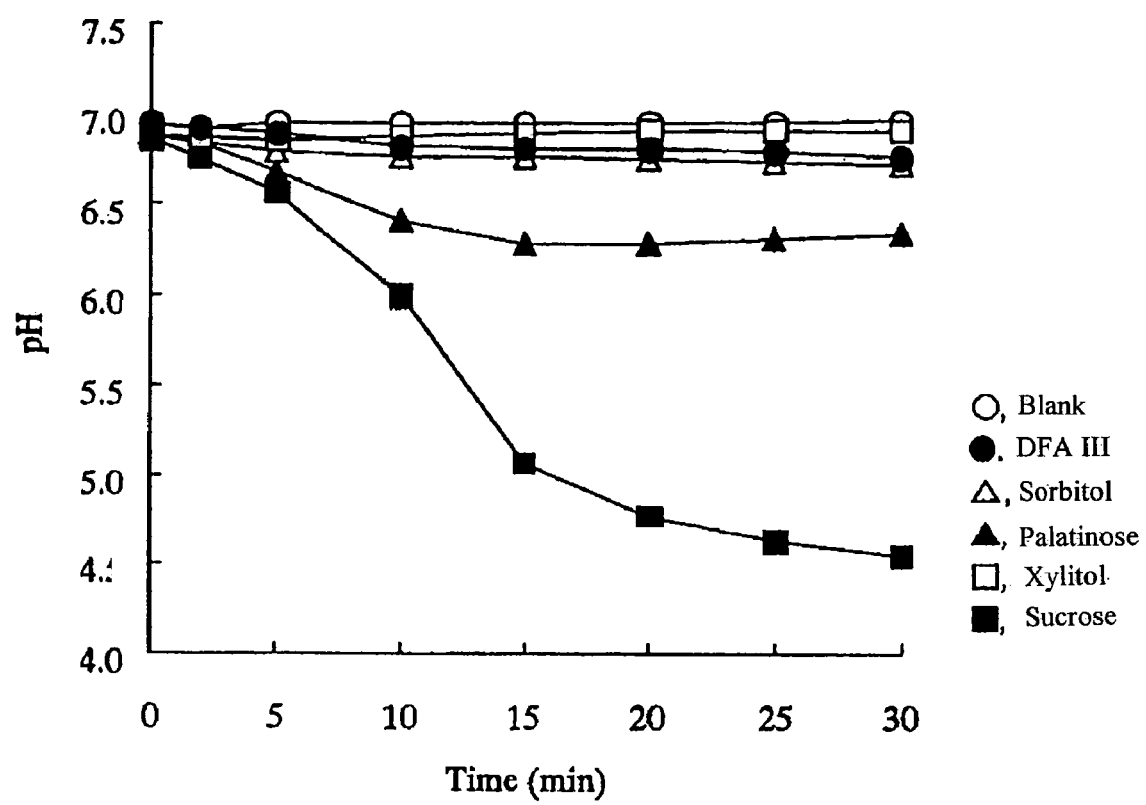
FIG. 6 shows change with time in the pH of reaction solutions in which DFA III, sorbitol, palatinose, xylitol, and sucrose were each added to the culture of dental caries causative bacteria.

Dental caries causative bacteria (*Streptococcus mutans*) MT 8148 and 6715 strains provided by a microbial lineage storage laboratory of The Institute of Physical Chemical Research (Riken) were cultured on a brain heart infusion broth medium overnight and then cells were collected by centrifugation. The cells were washed twice with a phosphate buffered (5 mM) physiological saline solution (pH 7.0) and then suspended in the same saline solution. Ten milliliters each of 5% DFA III, sorbitol, palatinose, xylitol, and sucrose solutions were added to 2 ml of this concentrated cell suspension. Immediately, reaction was carried out at 37° C. and then change with time in pH of each reaction mixture was measured. As a result, it was shown that sucrose evidently lowered the pH with time, but DFA III produced almost no acid similarly to xylitol, sorbitol and palatinose that have no dental caries causing activity. Strain MT 6715 showed similar results. FIG. 6 shows results of the pH measurement with time for strain MT 8148.

Example 10

Effect of DFA and Sugar Alcohol in Inhibiting Acid Production by *Streptococcus mutans*

Figure 7:
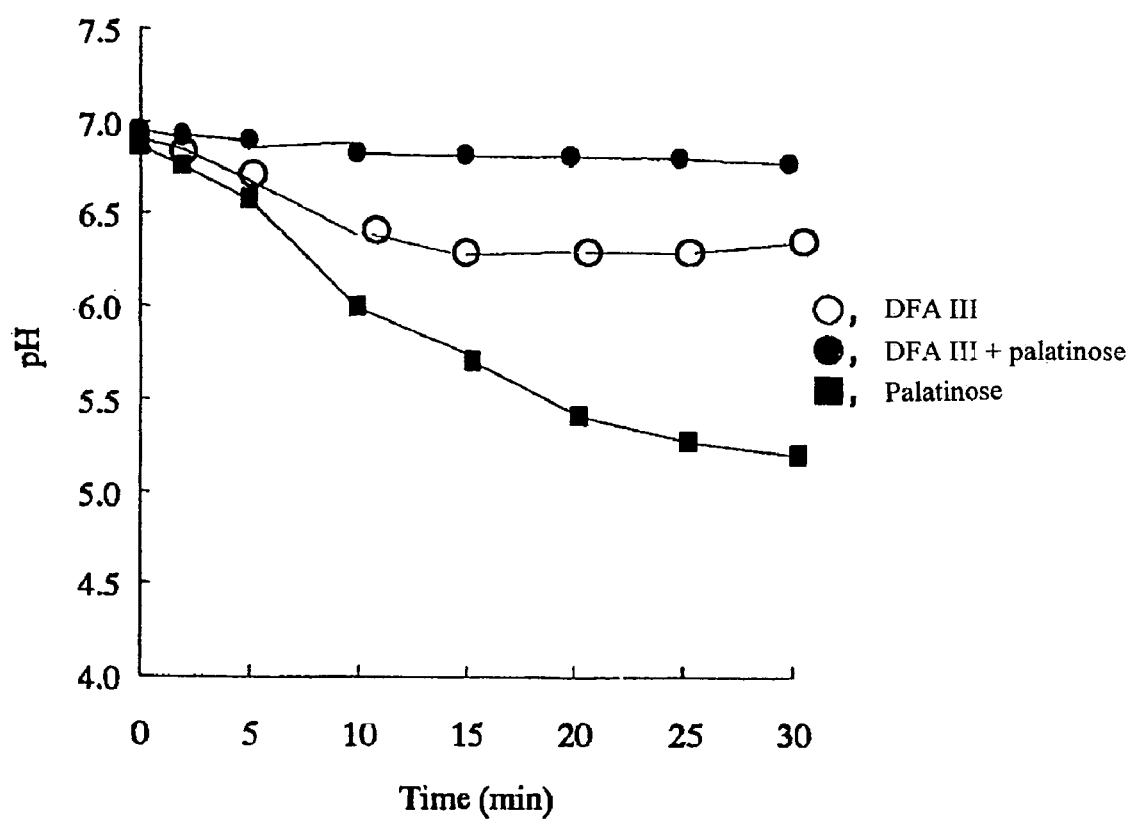
FIG. 7 shows change with time in the pH of reaction mixtures in which DFA III or palatinose alone, or both DFA III and palatinose were each added to the culture of dental caries causative bacteria.

Dental caries causative bacteria (*Streptococcus mutans*) MT 8148 and 6715 strains provided by a microbial lineage storage laboratory of The Institute of Physical Chemical Research (Riken) were cultured on a brain heart infusion broth medium overnight and then cells were collected by centrifugation. The cells were washed twice with a phosphate buffered (5 mM) physiological saline solution (pH 7.0) and then suspended in the same saline solution. Ten milliliters each of a 1% palatinose solution, 1% DFA III, a 1% palatinose solution with 1% DFA III added were added to 2 ml of this concentrated cell suspension. Immediately, reaction was carried out at 37° C. and then change with time in pH of each reaction mixture was measured. As a result, it was shown that acid was produced with 1% palatinose while almost no acid was produced in solutions added with 1% DFA III and 1% palatinose plus 1% DFA III. Strain MT 6715 showed similar results. FIG. 7 shows test results with strain MT 8148.

Example 11

Examples for preparing compositions are shown as follows:

| (1) Tooth paste | |
|---|---|
| Calcium carbonate | 30.00% by mass |
| Glycerin | 30.00 |
| Anhydrous silicic acid | 10.00 |
| DFA III | 2.00 |
| Sodium carboxymethyl cellulose | 1.00 |
| Sodium lauryl sulfate | 1.00 |
| Perfume | 0.01 |
| Purified water | Balance |
| Total | 100.00% by mass |

[Method of Preparation] Tooth paste was prepared based on the abovementioned composition according to an ordinary method.

| (2) Mouth wash | |
|---|---|
| Sorbitol | 30.00% by mass |
| Ethanol | 8.00 |
| DFA III | 0.10 |
| Sucrose fatty acid ester | 1.00 |
| Purified water | Balance |
| Total | 100.00% by mass |

[Method of Preparation] Mouth wash was prepared based on the abovementioned composition according to an ordinary method.

| (3) Tablet candy | |
|---|---|
| DFA II | 20.00% by mass |
| Xylitol | 5.00 |
| Palatinose | 5.00 |
| Erythritol | 5.00 |
| Lactose | 60.00 |
| Glycerin fatty acid ester | 0.20 |
| Purified water | Balance |
| Total | 100.00% by mass |

[Method of Preparation] According to an ordinary method.

| (4) Chewing gum | |
|---|---|
| Gum base | 20.00% by mass |
| Xylitol | 40.00 |
| Palatinose | 20.00 |
| Erythritol | 9.00 |
| DFA III | 10.00 |
| Softening agent | 1.00 |
| Total | 100.00% by mass |

[Method of Preparation] According to an ordinary method.

Reference to Biological Material Deposited

*Arthrobacter* sp. AHU 1753 strain has been deposited at the following institute:

The International Patent Organism Depositary, National Institute of Advanced Industrial Science and Technology, Central 6, 1-1, Higashi, Tsukuba-shi, Ibaraki-ken, Japan Depository number: FERM BP-8296

Depository date: Feb. 18, 2003

POSSIBLE INDUSTRIAL APPLICATION

As mentioned above, a composition of the present invention is suitable for use in accelerating the absorption of magnesium, zinc or copper, accelerating bone formation, accelerating diuretic action, improving bowel movement and inhibiting dental caries.

What is claimed is:

1. A composition for inhibiting the induction of dental caries, which comprises a combination of difructose anhydride III and palatinose in amounts effective to inhibit the induction of dental caries, wherein the amount of difructose anhydride III is 1% by weight.

2. A toothpaste or mouthwash for inhibiting the induction of dental caries, which comprises the composition according to claim 1.

3. A chewing gum or tableted candy for inhibiting the induction of dental caries, which comprises the composition according to claim 1.

* * * * *